United States Patent
Dormady et al.

(10) Patent No.: US 9,572,773 B2
(45) Date of Patent: Feb. 21, 2017

(54) LAYERED DRUG DELIVERY DEVICE

(75) Inventors: Daniel Dormady, Gretna, NE (US); Steve Jurgens, Filley, NE (US)

(73) Assignee: Novartis A.G., Basel (CH)

( * ) Notice: Subject to any disclaimer, the term of this patent is extended or adjusted under 35 U.S.C. 154(b) by 1543 days.

(21) Appl. No.: 12/767,468

(22) Filed: Apr. 26, 2010

(65) Prior Publication Data

US 2011/0262520 A1    Oct. 27, 2011

(51) Int. Cl.
| | |
|---|---|
| *A61K 9/70* | (2006.01) |
| *A61K 9/00* | (2006.01) |
| *A61K 31/4439* | (2006.01) |

(52) U.S. Cl.
CPC ........... *A61K 9/006* (2013.01); *A61K 31/4439* (2013.01); *A61K 9/7007* (2013.01); *A61K 9/7023* (2013.01)

(58) Field of Classification Search
None
See application file for complete search history.

(56) References Cited

U.S. PATENT DOCUMENTS

| | | |
|---|---|---|
| 4,517,173 A | 5/1985 | Kizawa et al. |
| 4,572,832 A | 2/1986 | Kigasawa et al. |
| 4,713,243 A | 12/1987 | Schiraldi et al. |
| 4,900,554 A | 2/1990 | Yanagibashi et al. |
| 5,137,729 A | 8/1992 | Kuroya et al. |
| 6,585,997 B2 * | 7/2003 | Moro et al. .................... 424/434 |
| 6,787,157 B1 * | 9/2004 | Rosenberg et al. ........... 424/486 |
| 6,797,283 B1 * | 9/2004 | Edgren et al. ................. 424/472 |
| 2001/0051186 A1 | 12/2001 | Acharya et al. |
| 2002/0132005 A1 * | 9/2002 | Faour ............................ 424/473 |
| 2003/0219479 A1 * | 11/2003 | Chen et al. .................... 424/466 |
| 2004/0006111 A1 | 1/2004 | Widder et al. |
| 2005/0079220 A1 * | 4/2005 | Yu et al. ....................... 424/473 |

FOREIGN PATENT DOCUMENTS

WO    WO 2007112286 A2 * 10/2007

OTHER PUBLICATIONS

EUDRAGIT(R) Time-Controlled Drug release page, accessed May 14, 2013.*

* cited by examiner

*Primary Examiner* — Nissa Westerberg
(74) *Attorney, Agent, or Firm* — William R. Majarian; Joshua C. Sanders

(57) ABSTRACT

The layered drug delivery devices of the present invention have an outer side and an inner side. The device includes, in order from the outer side to the inner side, a first layer and a second layer. The first layer wherein the first layer is water insoluble, water swellable, and water permeable. The second layer includes a therapeutic amount of a water soluble drug and a water soluble mucoadhesive film. The second layer is disposed such that water passing through said first layer solubilizes the drug. The said solubilized drug then can permeate through a mucosal membrane when the inner side is in contact with the mucosal membrane. The drug delivery device is in sheet form.

21 Claims, 7 Drawing Sheets

10

LAYERED DRUG DELIVERY DEVICE

BACKGROUND OF THE INVENTION

The present invention relates to a layered drug delivery device in thin sheet form for oral/buccal transmucosal delivery of active drug to a human or animal.

The delivery of active substances into the blood stream poses a large challenge in the pharmaceutical sciences. Oral administration of pharmaceutical compositions has drawbacks including difficulty in keeping the active in a desired location for absorption, loss of drug due to decomposition in the acidic environment of the stomach, and reduced bioavailability due to metabolism of the active in the liver, poor solubility, and/or efflux.

There has been much interest in drug delivery through the oral mucosa. The buccal, gingival (e.g. gums, palate (e.g. roof of mouth), and sublingual (e.g. under-tongue) membranes offer several advantages for active delivery as compared to typical oral administration of the active. For example, actives administered through the oral mucosa have rapid onset of action, reach high concentration in the blood in short periods of time, avoid first-pass effect of hepatic metabolism, and avoid exposure of the drug to fluids of the gastrointestinal tract.

U.S. Pat. Nos. 4,517,173; 4,572,832; 4,713,243; 4,900,554 and 5,137,729 and Published US Patent Applications Nos. 2001/0051186 and 2004/0006111, all of which are incorporated herein for all purposes, describe delivering active substances through a mucosal membrane using thin film compositions. However, there is still a need for drug delivery device that allows for the delivery of unstable and/or hard to dissolve active ingredients through the mucosal membrane.

SUMMARY OF THE INVENTION

The present invention provides a layered drug delivery device that is in thin sheet form and has an outer side and an inner side. The device comprises in order from the outer side to the inner side: a first layer wherein the first layer is water insoluble, water swellable, and water permeable at least when in the swelled state, and a second layer comprising a therapeutic amount of a water soluble drug and a water soluble mucoadhesive film. The second layer is disposed such that water passing through said first layer solubilizes the drug, wherein said solubilized drug can permeate through a mucosal membrane when the inner side is in contact with the mucosal membrane.

DETAILED DESCRIPTION OF THE INVENTION

Numerical values in the specification and claims of this application, particularly as they relate to polymeric materials, reflect average values for a composition that may contain individual polymer molecules of different characteristics. Furthermore, the numerical values should be understood to include numerical values which are the same when reduced to the same number of significant figures and numerical values which differ from the stated value by less than the experimental error of the measurement technique used to determine the value Reference throughout the specification to "one embodiment," "another embodiment," "an embodiment," "some embodiments," and so forth, means that a particular element (e.g., feature, structure, property, and/or characteristic) described in connection with the embodiment is included in at least one embodiment described herein, and may or may not be present in other embodiments. In addition, it is to be understood that the described element(s) may be combined in any suitable manner in the various embodiments.

In order to provide a preferable drug delivery device in thin sheet form, the thin sheet has several important characteristics, namely:

(1) the ability to carry sufficient drug to provide a therapeutic dose in a strip of a size considered acceptable to a user. Strips that have too little carrying capacity require too large a strip, or the use of too many strips to be considered acceptable by the consumer.

(2) conditions allowing for buccal permeation time in the mouth that is appropriate to the delivery of active through the oral mucosa. Too long of permeation time results in insufficient blood levels to reduce or control symptoms.

(3) the capability of being formed into a thin strip without substantial degradation and/or loss of the active in the original formulation.

(4) the ability to prevent degradation and loss of the active over time. The thin strip should have a suitable shelf life so that it can be manufactured, transported, and sold to a consumer while maintaining the desirable properties described herein.

(5) the ability to provide an active ingredient in solution form such that the active can permeate across the mucosal surface and into the blood stream.

(6) the ability to allow drug to dissolve in saliva. Many drug require a specific pH range for dissolution and the pH environment of the absorption site and active layer should be maintained with the desired range.

(7) ability to maintain drug in a preferred form to favor permeation. Uncharged forms of drugs generally have a higher permeability than charged or salt forms. This is often a function of pH environment and is dependent upon the drug.

(8) ability to retain dissolved drug at high concentration in close proximity to oral mucosa and to prevent washing away and swallowing of the drug.

Figure 1:
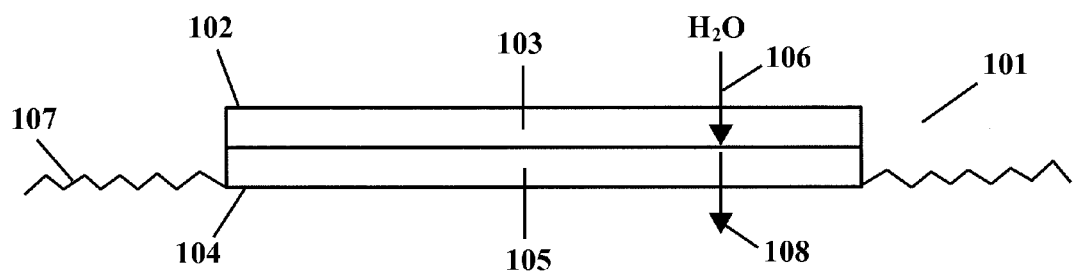
FIG. 1 is a side view of a layered drug delivery device.

The Drug Delivery Device:

The drug delivery devices of the present invention provides these benefits and many others. As shown in FIG. 1, the layered drug delivery devices 101 of the present invention have an outer side 102 and an inner side 104. In one embodiment shown in FIG. 1, the device 101 includes, in order from the outer side 102 to the inner side 104, a first layer 103 and a second layer 105. The first layer 103 is water insoluble, water swellable, and water permeable at least when in the swelled state. The second layer 105 includes a therapeutic amount of a water soluble drug and a water soluble mucoadhesive film. The second layer 105 is disposed such that water passing through 106 said first layer solubilizes the drug. The said solubilized drug then can permeate 108 through a mucosal membrane 107 when the inner side 104 is in contact with the mucosal membrane 107.

The First Layer 103

The first layer 103 of the drug delivery device 101 is water insoluble, water swellable, and water permeable at least when in the swelled state. Water/saliva may flow through the first layer to hydrate the second layer. Even though the first layer 103 is insoluble in water this does not mean that the first layer will not disintegrate over time. In a preferred embodiment the first layer will disintegrate after at least 50 wt %, more preferably at least 75 wt % and most preferably at least 90 wt % (e.g. more than 95 wt %) of the drug originally contained in the second layer has permeated through the mucosal membrane.

The components of the first layer 103 are not particularly limited. In one embodiment described below, a first layer satisfying the requirements above will be a thin film having a water insoluble, water swellable, and water permeable film forming polymer composition, a water soluble film forming agent, a pore forming agent and a low molecular weight plasticizer. In a broad sense according to the present embodiment the first thin film layer will comprise: 25 to 85 wt % of a water insoluble, water swellable, and water permeable film forming polymer composition; 1 to 75 wt % of a water soluble film forming agent; 5 to 50 wt % of a pore forming agent; and 1 to 20 wt % of a low molecular weight plasticizer. In a more preferred embodiment the first thin film layer will comprise: 35 to 75 wt % of a water insoluble, water swellable, and water permeable film forming polymer composition; 2 to 65 wt % of a water soluble film forming agent; 5 to 20 wt % of a pore forming agent; and 5 to 15 wt % of a low molecular weight plasticizer. In a sometimes yet more preferred embodiment the first thin film layer will comprise: 54 to 63 wt % of a water insoluble, water swellable, and water permeable film forming polymer composition; 6 to 19 wt % of a water soluble film forming agent; 10 to 15 wt % of a pore forming agent; and 8 to 12 wt % of a low molecular weight plasticizer.

The water insoluble, water swellable, and water permeable film forming polymer composition is not particularly limited and can be made up of any film forming polymer(s)/polymer composition that exhibits these properties. For example a neutral copolymer based on ethyl acrylate and methyl methacrylate sold under the tradename EUDRAGIT® (NE 30D, L100, S100, or the like) or a polyvinyl acetate polymer stabilized with povidone and sodium lauryl sulfate which is sold under the trade name Kollicoat® SR30D may be used. Kollicoat SR 30 D is an aqueous dispersion consisting of 27% polyvinyl acetate stabilized with 2.7% povidone and 0.3% sodium lauryl sulfate. It is a low viscosity, milky white, or slightly yellowish dispersion with a weak characteristic odor. It has been used in the past as an controlled release coatings for tablets. The present Inventors found that this particular composition is particularly preferred for use in forming the sheet-like drug delivery devices of the present invention.

The water soluble film forming agent is not particularly limited and can be made up of any film forming agent that is water soluble. In a preferred embodiment this component of the first layer will also have mucoadhesive properties. In some embodiments the water soluble film forming agent is a hydrophilic polymer material or mixture of polymers which can adhere to wet mucosal surfaces. Examples of suitable polymers include hydroxypropyl cellulose, hydroxypropyl methylcellulose (e.g. hypromellose or HPMC), hydroxy ethylcellulose, carboxymethyl cellulose, dextran, guar-gum, polyvinyl pyrrolidone, pectins, starches, gelatin, acrylic acid copolymers, vinyl polymers, vinyl copolymers, vinyl alcohols, alkoxy polymers, polyethylene oxide polymers, polyethers, and the like. Of these exemplary water soluble film forming agents hypromellose and polyethylene oxide based polymers alone or in combination are most often preferred.

Hypromellose (HPMC) is available under the tradename METHOCEL™ from the Dow Chemical Company. These products are water-soluble cellulose ethers. The following table, from Dow Chemical, exemplifies some of the characteristics of these polymers.

| METHOCEL ™ Product Name | Chemical Type[1] | Methoxyl Content, % | Hydroxypropyl Content, % | Viscosity of 2% solution in water, cps @ 20° C. |
|---|---|---|---|---|
| METHOCEL ™ E3 | Hypromellose 2910 | 28-30 | 7-12 | 2.4-3.6 |
| METHOCEL ™ E5 | Hypromellose 2910 | 28-30 | 7-12 | 4-6 |
| METHOCEL ™ E6 | Hypromellose 2910 | 28-30 | 7-12 | 5-7 |
| METHOCEL ™ E50 | Hypromellose 2910 | 28-30 | 7-12 | 40-60 |
| METHOCEL ™ E4M | Hypromellose 2910 | 28-30 | 7-12 | 3000-5600 |
| METHOCEL ™ E10M | Hypromellose 2910 | 28-30 | 7-12 | 7500-14,000 |
| METHOCEL ™ K3 | Hypromellose 2208 | 19-24 | 7-12 | 2.4-3.6 |
| METHOCEL ™ K100 | Hypromellose 2208 | 19-24 | 7-12 | 80-120 |
| METHOCEL ™ K4M | Hypromellose 2208 | 19-24 | 7-12 | 3,000-5,600 |

In the first layer a combination of a low/mid range viscosity (e.g. Methocel E50) and high viscosity MethocelK4M) were found to be provide desirable properties. When used in combination the weight ratios of the combinations can be from 20/1 to 1/20 and more preferably 10/1 to 1/10 (e.g. 5/1 or 1/5).

Polyethylene oxide (PEO) suitable for use in the first layer of the present embodiment preferably has a molecular weight of from 70,000 to 300,000 daltons, for example 100,000 to 200,000 daltons (e.g. preferably about 100,000 daltons). PEO with these characteristics is available from Dow Chemical as POLYOX™ WSR N-10 (Mw about 100,000 Daltons) and POLYOX™ WSR N-80 (Mw about 200,000 Daltons). Of these, POLYOX™ WSR N-80 is frequently preferred. Significantly higher molecular weight PEO (e.g up to 7,000,000 Daltons or more), or compositions that include coagulants that cause an increase in molecular weight of the polyethylene oxide may also be used in other embodiments. For example where extended release of the drug is desired, higher molecular weight PEO may be desired to prolong the integrity of the layer.

When hypromellose and polyethylene oxide are used in combination as the water soluble film forming agent, the weight ratio of hypromellose to polyethylene oxide is not particularly limited and is preferably in a range of 1/20 to 20/1, and more preferably in a range of 1/10 and 10/1 (e.g. in a range of 1/5 and 5/1). In one embodiment the weight ratio is in a range of 1/2 to 2/1 (e.g. 1/1). It is noted that PEO is also referred to in the art as polyethylene glycol (PEG). However, since a low molecular weight plasticizer that may be PEG is also used in the composition, this component is referred to as PEO to maintain a distinction.

A pore former is also present in the first layer such that a porous matrix is created in the first layer to allow water (e.g. saliva) to travel through the first layer to hydrate the second layer. The interaction between the viscous and hydrated second layer and the first layer minimizes the ability of solublized API in the second layer from leaching through the first layer. This is important to prevent drug from being washed away from the membrane and swallowed rather than absorbed. Furthermore this is important to prevent the some times unpleasant tasting drug from leaching into the oral cavity and away from the membrane.

The pore forming agent of the first layer is likewise not particularly limited. It preferably easily and readily dissolves or disintegrates in water to create the porous matrix to allow saliva to quickly travel through the first layer to solubilize the drug in the second layer. In one embodiment the pore former is low-molecular weight and water soluble carbohydrate or water soluble hydrogenated carbohydrate, such as maltodextrin and the like. In another embodiment the pore former comprises a readily soluble polymer such as a polymerized form of vinylpyrolidone (e.g. PVP or povidone). In other embodiments, a combination of pore formers may be used (e.g. maltodextrin and PVP or povidone).

In other embodiments the pore forming agent is a water-soluble polyol (e.g. a sugar alcohol). Specific and non-limiting examples of sugar alcohols useful for this purpose include sorbitol, xylitol, mannitol, lactitol, and maltitol. In other embodiments erythritol may optionally be used as the sugar alcohol or in combination with other sugar alcohols. Of these sorbitol (melting point 95° C.) and mannitol (melting point 167° C.) are particularly preferred, with mannitol being most preferred.

Without intending to be bound by any particular mechanism, it is believed that controlling the type and amount of the pore former and water soluble film forming agent is effective to also control the disintegration rate of the thin strips. Therefore, it is preferred to select the type and amount of these components such that a significant portion (e.g. 80 wt % or more, or 90 wt % or more) of the API is delivered through the mucosal membrane prior to complete disintegration of the strip.

The first layer of the present embodiment also includes a low molecular weight plasticizer. Such plasticizers include glycerin, propylene glycol, triethyl citrate, and low molecular weight (e.g. less than 4000 Dalton) polyethylene glycol (PEG). In a preferred embodiment the low molecular weight plasticizer is Propylene glycol.

The first layer 103 may include a myriad of additional excipients or additives such as colorants, stabilizers, and flavorants. The addition of these excipients or additives is well known in the art and does not depart from the scope of the present invention.

The Second Layer 105:

The second layer 105 includes a therapeutic amount of a water soluble drug and a water soluble mucoadhesive film containing a water soluble film forming agent. The second layer 105 is disposed such that water passing through 106 said first layer 103 hydrates the second layer and solubilizes the drug. The solubilized drug then can permeate 108 through a mucosal membrane 107 when the inner side 104 is in contact with the mucosal membrane 107.

The second layer is preferably present as a solid solution. Water passing through the first layer and to a generally lesser extent water from the surface of the oral mucosa hydrates the second layer and preferably turns it into a viscous liquid or gel form. A solid solution is a solid-state solution (or a molecular dispersion) of one or more solutes in a solvent (e.g. acetone and/or water). Such a mixture is considered a solution rather than a compound when the crystal structure of the solvent remains unchanged by addition of the solutes, and when the mixture remains in a single homogeneous phase.

The water soluble drug is a water soluble active pharmaceutical ingredient adapted for transmucosal absorption into the blood stream and is not particularly limited. The term "water soluble" as it applies to the description of the drug means that at least a portion of the drug dissolves in water. The amount of solubility of the active can depend upon the pH of water. For example as explained below, the water may contain a pH modifier and/or solubility enhancer to adjust the pH or increase solubility of the drug so that a portion of the drug may dissolve in water. The drug may be selected from among any group wherein a transmucosal administration of the drug over a period ranging from, for example, a minute to several hours is desired. The drug may be selected from among analgesic, anorexic, antiarthritic, antibacterial, antibiotic, anticonvulsant, anti-depressant, antidiabetic, antifungal, antihistaminic, anti-hypertensive, anti-inflammatory, anti-neoplastic, antiparkinsonism, antipyretic, anticholinergic, anesthetic, antimicrobial, antiviral, anti-ulcer, bronchodilator, cardiovascular, contraceptive, central nervous system affecting, ionotropic, vasodilator, vasoconstrictor, decongestant, diuretic, erectile dysfunction, hypoglycemic, hormone, hypnotic, hematinic, electrolyte supplement, germicidal, muscle relaxant, parasympathetolytic, parasympathetomimetic, proton pump inhibitor, tranquilizer, ophthalmic, psychostimulant, vitamin, and the like drugs. In a preferred embodiment the drug is water soluble proton pump inhibitor selected from the group consisting of lansoprazole, omeprazole, esomeprazole, rabeprazole, patoprazole, pariprazole, tentaprazole, and leminoprazole. Of these lansoprazole which is sold under the tradename Prevacid® is particularly preferred.

The water soluble film forming agent of the second layer 105 is not particularly limited and can be made up of any film forming agent that is water soluble. In preferred embodiments the water soluble film forming agent exhibits mucoadhesive properties itself. Where it does exhibit mucoadhesive properties additional mucoadhesive agents need not, but are preferably added to increase the mucoadhessive properties of the layer. In some embodiments the water soluble film forming agent is a hydrophilic polymer material or mixture of polymers which can adhere to wet mucosal surfaces. Examples of suitable water soluble film forming polymers include hydroxypropyl cellulose, hydroxypropyl methylcellulose (e.g. hypromellose or HPMC), hydroxy ethylcellulose, carboxymethyl cellulose, dextran, guar-gum, polyvinyl pyrrolidone, pectins, starches, gelatin, acrylic acid copolymers, vinyl polymers, vinyl copolymers, vinyl alcohols, alkoxy polymers, polyethylene oxide polymers, polyethers, and the like.

Of these exemplary water soluble film forming agents hypromellose and polyethylene oxide based polymers alone or in combination are most often preferred. The type of polyethylene oxide based polymers that are suitable for use in the second layer are the same as described above with regard to first layer. POLYOX™ WSR N-80 (Mw about 200,000 Daltons) is likewise a preferred polyethylene oxide. Significantly higher molecular weight PEO (e.g up to 7,000,000 Daltons or more), or compositions that include coagulants that cause an increase in molecular weight of the polyethylene oxide may also be used in other embodiments.

For example where extended release of the drug is desired, higher molecular weight PEO may be desired to prolong the integrity of the layer.

As described above hypromellose (HPMC) suitable for use in the present invention is available under the tradename METHOCEL™ from the Dow Chemical Company. It has been found that a low viscosity or combination of low viscosity hypromellose products (e.g. Methocel E3 and/or E5) provide desirable properties in the second layer of the layered device. In some embodiments, when used in combination the weight ratios of hypromellose of the combinations can be from 20/1 to 1/20 and more preferably 10/1 to 1/10 (e.g. 5/1 or 1/5), for example about 1/1.

When hypromellose and polyethylene oxide are used in combination as the water soluble film forming agent, the weight ratio of hypromellose to polyethylene oxide is not limited and may be in a range of 1/20 to 20/1, or 1/10 to 10/1, and more preferably in a range of 1/5 and 5/1. In one embodiment the weight ratio is in a range of 1/2 to 2/1 (e.g. 1/1). It is noted that PEO is also referred to in the art as polyethylene glycol (PEG). However, since a low molecular weight plasticizer that may be PEG is also used in the composition, this component is referred to as PEO to maintain a distinction.

In one embodiment the second layer 105 includes other ingredients and is a thin film containing: 1 to 50 wt % of a water soluble drug (e.g. API), 1 to 75 wt % of a water soluble film forming agent, 0.1 to 50 wt % of a water soluble mucoadhesive agent, 1 to 50 wt % of a permeation enhancer, 0.1 to 10 wt % of pH modifier, and 1 to 20 wt % of a low molecular weight plasticizer. In a sometimes more preferred embodiment the second layer is a thin film containing: 10 to 25 wt % of a water soluble drug (e.g. API), 25 to 60 wt % of a water soluble film forming agent, 0.3 to 25 wt % of a water soluble mucoadhesive agent, 5 to 40 wt % of a permeation enhancer, 1 to 7.5 wt % of pH modifier, and 2.5 to 10 wt % of a low molecular weight plasticizer. In a yet sometimes more preferred embodiment the second layer is a thin film containing: 14 to 20 wt % of a water soluble drug (e.g. API), 35 to 50 wt % of a water soluble film forming agent, 1 to 5 wt % of a water soluble mucoadhesive agent, 15 to 30 wt % of a permeation enhancer, 2.5 to 5 wt % of pH modifier, and 5 to 7 wt % of a low molecular weight plasticizer.

As discussed above the water soluble film forming agent need not be, but preferably is, mucoadhesive itself. In either case a water soluble mucoadhesive agent is preferably added to the second layer or as a separate layer disposed on the inner side of the device. The water soluble mucoadhesive agent is a compound that adheres to a mucous membrane. In a preferred embodiment the mucoadhesive agent is a hydrophilic polymer, natural or synthetic, which is adhesive to mucosal surfaces. In another embodiment the mucoadhesive agent is a hydrogel, natural or synthetic, which is adhesive to mucosal surfaces. Mucoadhesive hydrophilic polymer films are known in the art and some may preferably be used as the "water soluble film forming agent" in the first and second layers of the delivery device. However, in order to maintain a distinction between the "water soluble mucoadhesive agent" discussed here and the "water soluble film forming agent discussed above" it is noted that regardless of whether the water soluble film forming agent has mucoadhesive properties, the second layer (or third layer disposed toward the inner side of the second layer) will preferably include an additional, separate, and distinct "water soluble mucoadhesive agent." Examples of suitable water soluble mucoadhesive agents include poly vinyl pyrrolidone (PVP), methyl cellulose (MC), sodium carboxy methylcellulose (SCMC), hydroxy propyl cellulose (HPC), other cellulose derivatives, carboxy vinyl polymer (also known as "acrylic acid polymers") that are cross linked using a divinyl glycol cross linker (e.g. polycarbophils) or an allyl ether of pentaerythritol as the cross linker (e.g. "Carbomer" such as carbomer 940, and carbomer 947P, carbomer 974P, carbomer 971P, and carbomer 71G), polyacrylates and their crosslinked and/or copolymerized modifications (e.g. water soluble PROLOC™ compositions), chitosan and its derivatives, eudragit, combinations thereof, and the like. Other examples of suitable mucoadhesive agents include dextran, guar-gum, starches, gelatin, casein, acrylic acid, acrylic acid esters, acrylic acid copolymers, vinyl polymers, vinyl copolymers, vinyl alcohols, alkoxy polymers, polyethylene oxide polymers, polyethers, thiopolymers, combinations thereof, and the like.

Of these exemplary mucoadhesive compounds carboxy vinyl polymers that are cross linked using an allyl ether of pentaerythritol as the cross linker (e.g. Carbomer 974P with a viscosity of 29,400 to 39,400 centi-Poise measured at 25° C.) or divinyl glycol (e.g. polycarbophil AA-1 USP has a viscosity of between 4,000 and 11,000 centi-Poise measured at 25° C.) are typically preferred.

Information from the manufacturer indicates that Carbopol 974P has the properties in the following table:

| Test | Specification | Lot Test Frequency[1] | Test Procedure[2] |
| --- | --- | --- | --- |
| Identification | | | |
| Colorimetric test | Pass | 1:200 | USP/NF; Ph. Eur. |
| Gel formation test | Pass | 1:1 | USP/NF; Ph. Eur. |
| Infrared spectrum | Pass | —[3] | Ph. Eur.; JPE |
| Precipitate test | Pass | 1:200 | Ph. Eur. |
| Carboxylic Acid Content, Assay % | 56.0-68.0[4] | 1:1 | USP/NF |
| Viscosity, cP, 25° C. | | | |
| Brookfield RVT, 20 rpm, neutralized to pH 7.3-7.8 0.5 wt % mucilage, spindle #6 | 29,400-39,400 | 1:1 | USP/NF; Ph. Eur. |
| Loss on Drying, % | 2.0 max | 1:1 | USP/NF |

-continued

| Test | Specification | Lot Test Frequency[1] | Test Procedure[2] |
|---|---|---|---|
| Heavy Metals, ppm | | | |
| Total heavy metals, as Pb | 20 max | 1:200 | USP/NF |
| Specific metals: Hg, Pb, As, Sb | 10 max | 1:200 | Lubrizol SA-012 |
| Residual Solvent[5] | | | |
| Ethyl acetate, % | 0.50 max | 1:1 | Lubrizol SA-009 |
| Benzene, ppm | 0.50 max | 1:1 | Ph. Eur. |
| Residual Monomer, ppm | | | |
| Free acrylic acid | 1,000 max | 1:1 | Lubrizol SA-005 |
| Sulphated Ash, % (Residue on ignition) | 2.5 max | 1:200 | Ph. Eur.; JPE |
| pH, 0.2% Dispersion | 2.5-4.0 | 1:200 | JPE |

Information from the manufacturer indicates that Noveon® Polycarbophil AA-1 USP has the properties in the following table:

| Test | Specification | Lot Test Frequency[1] | Test Procedure[2] |
|---|---|---|---|
| Identification | | | |
| Colorimetric test | Pass | 1:200 | USP/NF |
| Gel formation test | Pass | 1:1 | USP/NF |
| Absorbing Power, g/g | 62 min | 1:1 | USP/NF |
| Viscosity, cP, 25° C. | | | |
| Brookfield RVT, 20 rpm, neutralized to pH 7.3-7.8 0.2 wt % mucilage, spindle #5 | 2,000-12,000 | 1:1 | Lubrizol 430-I[3] |
| Loss on Drying, % | 1.5 max | 1:1 | USP/NF |
| pH, 1% Dispersion | 4.0 max | 1:1 | USP/NF |
| Residual Solvent[4] | | | |
| Ethyl acetate, % | 0.45 max | 1:1 | Lubrizol SA-009 |
| Benzene, ppm | 0.50 max | 1:1 | Lubrizol SA-064 |
| Residual Monomer, ppm | | | |
| Free acrylic acid | 3,000 max | 1:1 | Lubrizol SA-005 |
| Sulphated Ash, % (Residue on ignition) | 4.0 max | 1:100 | USP/NF |

"Permeation enhancer" or similar terms mean a material that enhances the permeation of the water soluble drug through the mucossal membrane, and an "effective amount" of an enhancer means an amount effective to enhance penetration through the mucosa of the drug to a selected degree. Permeation enhancers are well-known in the art and they are not particularly limited for use in the present invention. Several permeation enhancers are also known to be solubilizing agents and make less soluble actives more soluble in water. In a preferred embodiment one of these known solublizing agents/permeation enhancers will be selected. For example several suitable permeation enhancers are described and disclosed in *Permeation Enhancers—How Do They Work*, Nicollazo et. al., Journal of Controlled Release 105 (2005) at pages 1-15. A non-limiting list of suitable permeation enhancers includes: enzymes such as papain, bromelain; terpenes such as menthol, camphor, and thymol; azone; fatty acids, their salts, and esters; lecithin; monoglycerides; triglycerides; chitosan and methylated chitosan; bile salts such as sodium glycocholate; cyclodextrins; non-ionic surfactants; ionic surfactants such as sodium lauryl sulfate; carbamers; oils such as cremophor RH40, PEG-40, and hydrogenated castor oil); solubilizer for hydrophobic pharmaceuticals such as fat-sol; vitamins; essential oils; non-ionic solubilizer & emulsifying agent; lutrol F68 (poloxamer 188); 2,3-Lauryl ether; phosphatidylcholine; aprotinin; polyoxyethylene; azone; polysorbate 80; benzalkonium chloride; polyoxyethylene; cetylpyridinium chloride; phosphatidylcholine; cetyltrimethyl ammonium bromide; sodium EDTA; cyclodextrin; sodium glycocholate; dextran sulfate; sodium glycodeoxycholate; glycol; sodium lauryl sulfate; dimethyl sulfoxide; lauric acid; sodium salicylate; lauric acid/propylene; sodium taurocholate; lysophosphatidylcholine; sodium taurodeoxycholate; menthol; and sulfoxides. In a preferred embodiment the permeation enhancer is selected from the group consisting of menthol, dimethyl sulfoxide (DMSO), sodium glycocholate, monoglycerides, azone, and cyclodextrins, The second layer also preferably includes a pH modifier. The pH modifier is preferably added to control the pH at the mucosal membrane to be in a range where the water soluble drug is stable, is most soluble, maintained in solution, and/or where permeation across the mucosal membrane is promoted. Where for example the water soluble drug is a proton pump inhibitor (e.g. lansoprazole), controlling the pH at the absorption surface at greater than 8 is desired. The drug is stable and found to be maintained in solution at a high/basic pH of between 8 and 11 (e.g. more preferably between 8.5 and 10.5). To maintain the pH at the mucosal/buccal membrane at this pH range a base modifier is added. pH modification and science is extremely well known in the art, and the present invention is not limited by a particular modifier or method of modification. Where a base modifier is used in the present invention, NaOH is typically preferred due to its effectiveness as a pH modifier and its cost. Where a acidic modifier is used it is preferably selected from the group consisting of citric acid, hydrochloric acid, aspartic acid, and glutamic acid. It is important to select a pH modifier and an amount so as to create a preferred dissolution and absorption profile while minimizing the negative effect of high or low pH environment on the oral mucosa.

The second layer also preferably includes a low molecular weight plasticizer. Such plasticizers include glycerin, propylene glycol, triethyl citrate, and polyethylene glycol (PEG). In a preferred embodiment the low molecular weight plasticizer is PEG, which is miscible with the PEO, having a weight average molecular weight (Mw) of between 100 and 4000 Daltons, more preferably between 300 and 600 Daltons (e.g. 400 Daltons or PEG 400 in liquid form). The PEG is present in an amount of 5 to 30 wt % of the formulation, more preferably between 7 and 15 wt % (e.g. 10 wt %) of the formulation.

Figure 2:
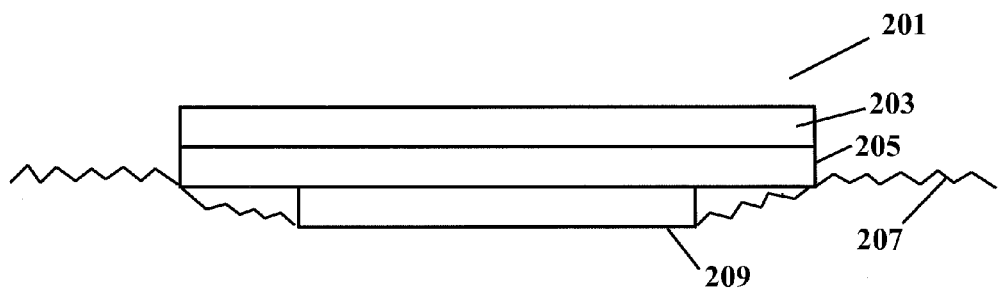
FIG. 2 is a side view of a layered drug delivery device.

In another embodiment and as shown in FIG. 2 the layered drug delivery device 201 contains a first 203 and second 205 layer. The first layer 203 is as described above and is water insoluble, water swellable, and water permeable. The second layer 205 comprises the water soluble drug and a mucoadhesive film forming compound. The layered drug delivery device also includes an optional additional layer(s) 209 (e.g. shown disposed on the inner side of the device in FIG. 2). In a preferred embodiment the optional additional layer(s) 209 includes a pH modifier, and/or a permeation enhancer, and/or a further water soluble mucoadhesive agent. Where there is more than one additional layer 209 (e.g. not shown) each additional layer 209 may contain a different component(s). In another embodiment the additional layer may be disposed between the first and second layer. This later embodiment may prove useful to provide a concentration gradient that drives a component (e.g. drug, permeation enhancer or pH stabilizer) toward or away from the mucosal membrane.

The second layer 105, 205 may include a myriad of additional excipients or additives such as colorants, stabilizers, and flavorants. The addition of these excipients or additives does not depart from the scope of the present invention.

Forming the Layered Drug Delivery Device:

The layered drug delivery devices of the present invention includes at least two layers or thin sheets (e.g. at least a first and second thin sheets), and potentially more layers/sheets, in planar contact. The layered drug devices may be formed and cut, as described below, from a master drug delivery device sheet into a size that is considered to be acceptable to a user. The master drug delivery device sheet is made up of at least two master thin sheets (e.g. the master first sheet and the master second sheet).

The method of forming the thin sheets is not particularly limited and they can be formed by, for example, solvent casting or melt extrusion or a combination thereof (e.g. the first sheet is solvent cast and the second sheet is extruded). In the case of melt extrusion it is preferred that the film forming compositions have a high molecular weight that allows for the extrusion and calendering of a thin sheet from the composition.

In a preferred embodiment, the master first and master second sheets are formed by solvent casting techniques where the sheet components described above are dissolved or suspended in a carrier solvent. The slurry or solution is then applied to a tray, or some other mold, having a large surface area where the solvent is driven off from the solution, and/or the sheet is cooled, leaving the desired components in thin film form. In the preferred embodiment described above where the second sheet is in solid solution form, the components of the second sheet are dissolved in an appropriate solvent (e.g. acetone and/or water) and then the solution is applied/coated to a tray or some other surface having a large surface area. During the solvent removal "drying" phase care could be taken to maintain the components in solution to provide a solid solution film. Here, as the solvent is removed the viscosity and % solids increases. The higher viscosity would prevent the drug and other excipients from self-associating or recrystallizing.

Once formed, the first and second master thin sheets may then be brought into contact with each other, optionally with the application of heat and/or pressure (e.g. laminated) to form the master drug delivery device sheet. The master drug delivery device sheet then can then be cut to form the individual layered drug delivery devices of the present invention. The amount of the water soluble drug/API in the delivery device will be a function of the size (length×width×thickness) of the layer of the device it is disposed in and the concentration of the drug in the layer. In a preferred embodiment, an individual layered drug delivery device (e.g. a single thin strip) will contain a recommended dose of the API. In preferred embodiments, the drug delivery device will be from 0.5 to 4 cm wide by 0.5 to 6 cm long. In other embodiments the drug delivery device will be from 1.5 to 3 cm wide (e.g. about 2 cm wide) by 1.5 to 5 cm long (e.g. about 3.5 cm long). In another embodiment, the drug delivery device preferably have dimensions of 22 mm×11 mm to 22 mm×37 mm. In another embodiment the drug delivery device is formed such that the total surface area of the strip is between 1 cm$^2$ to 20 cm$^2$ (e.g. between 1 cm$^2$ and 10 cm$^2$). Once in individual drug delivery device form the strips may be individually packaged or combined with others and packed in a multiple dose container (e.g. in ribbon/dispenser for stacked form).

The layered drug delivery device is preferably between 0.01 mm to 3.00 mm thick, for example between 0.1 mm to 2.00 mm thick (e.g. 0.1 mm to 1.00 mm thick). Preferably the width of the first layer divided by the width of the width of the second layer falls in a range of 1/10 to 10/1, more preferably in a range of 1/5 to 5/1, and more preferably 1/3 and 3/1 (e.g. about 1/1, about 1/2, or about 2/1). In another embodiment wherein first layer makes up 10 wt % to 90 wt % (e.g. 10 wt % to 50 wt %) of the layered drug delivery device and the second layer makes up 90 wt % to 10 wt % (e.g. 50 and 90 wt %) of the layered drug delivery device.

In the embodiments described herein, reference is made to at least two distinct thin sheet layers of the drug delivery device. Applicants note however, that there may be more than two distinct thin sheet layers. For example some of the ingredients of the first or second layer may be formed in a separate sheet and then co-laminated with the other sheets to form the combined delivery device.

Figure 3:
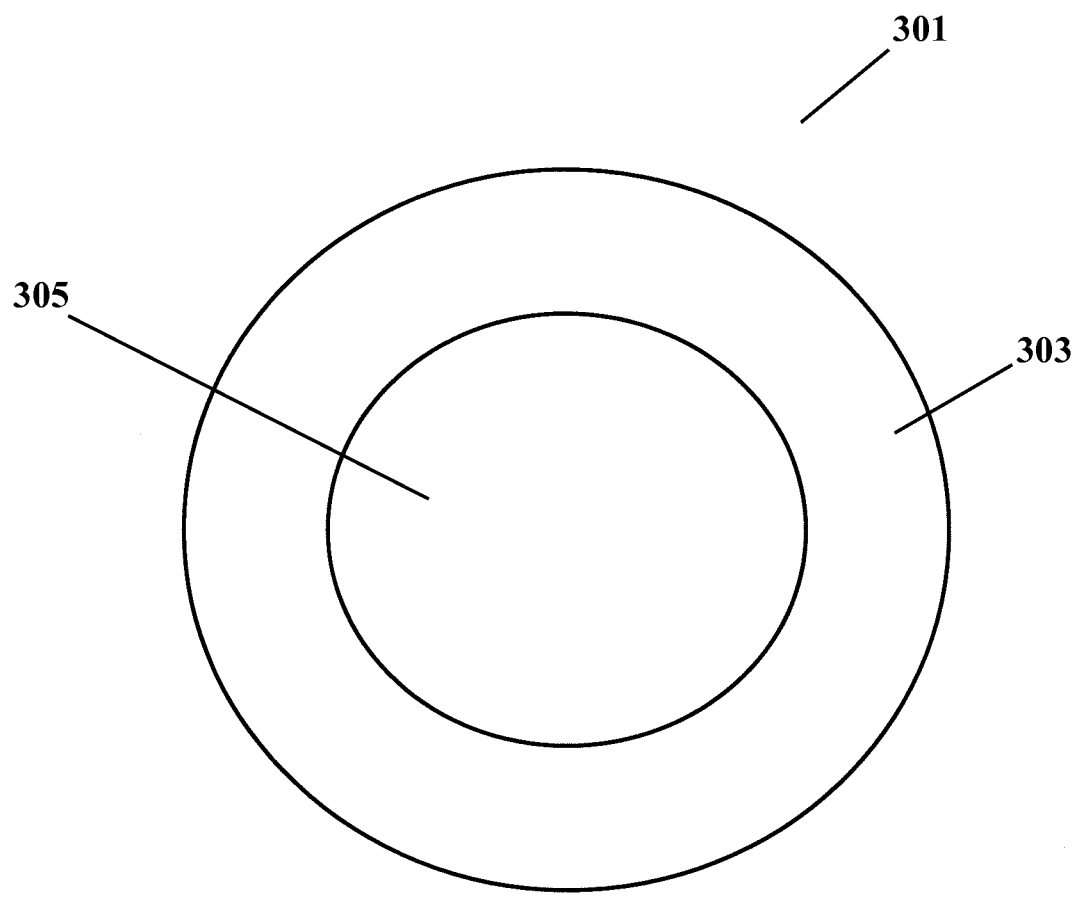
FIG. 3 is a bottom view of a layered drug delivery device.

The geometry of the individual layered drug device is not particularly limited other than it is in sheet form and can have any surface area dimensions. Preferably the flat surface dimension of the device is selected such that it fits comfortably within a user's mouth and it preferably does not contain any jagged or square edges. In a most preferably embodiment the surface area/shape of the device is circular, oval, or ovoid. In another preferred embodiment, shown in FIG. 3, the surface area of the first 303 and second 305 layers are selected such that the entire surface area of the second layer 305 is contained within the surface area of the first layer 303 of the layered device 301. In this embodiment it has been found that this is a preferable formation to prevent leaching of active out of the side of the combined device 301. This is further enhanced where the first layer 303 contains a water soluble film forming agent that is also mucoadhesive, wherein when applied to the mucosal membrane the entire second layer is sealed from the rest of the oral cavity. Water passing through the first layer preferably provides more 75%, more than 90%, more than 95% (e.g. 99%) of the water necessary to solubilize/wet the second layer with the remaining amount optionally coming from the area of the contacted oral mucosa itself.

EXAMPLES

Having described the invention in detail, the following examples are provided. The following examples provide acceptable and preferred strategies of forming test strips that are acceptable for use in industry. The examples should not be considered as limiting the scope of the invention, but merely as illustrative and representative thereof.

Illustration 1: In Vivo Testing

The following two bilayer drug delivery devices (variant 1 and variant 2) were prepared using standard solvent casting techniques to prepare each thin film layer. Two water soluble active drug layer film layers and one water permeable first layer were prepared using water and acetone as the solvent mixture. The components were dissolved in the water/acetone solvent and then introduced to a solvent casting sheet where solvent was driven off leaving the thin layers.

Water Soluble Active Layer Formula 1 (Expressed in % M/M Dry weight)

| Component | Quanity % (w/w) |
|---|---|
| Maisine - Glycerol mono-linoleate (PE) | 2.19 |
| Capryol 90 - Propylene glycol monocaprylate (PE) | 2.19 |
| Peceol - Glycerol - mono-oleate 4C-EP (PE) | 2.19 |
| Capryol pgmc - Propylene glycol monocaprylate (Type 1) (PE) | 2.19 |
| Labrafac PG - Propyleneglycol dicaprylocaprate | 2.19 |
| Labrasol - Caprylocaproyl polyoxylglycerides (PE) | 2.19 |
| Menthol (PE) | 3.24 |
| Dimethyl sulfoxide - DMSO (PE) | 8.69 |
| Sodium glycocholate (PE) | 3.24 |
| Macrogel 400 - Polyethylene glycol 400 | 5.42 |
| Methocel E5 - hypromellose | 16.15 |
| Methocel E3 - hypromellose | 22.19 |
| Polyethylene Oxide N80 | 3.67 |
| Proloc 25 | 4.51 |
| Sodium hydroxide (weight in comp 2.00N 8% (W/v)) | 3.8 |
| Lansoprazole | 15.94 |

(PE)—Permeation Enhancer

Water Soluble Active Layer Formula 2 (Expressed in % M/M Dry weight)

| Component | Quanity % (w/w) |
|---|---|
| Menthol (PE) | 5.1 |
| Dimethyl sulfoxide - DMSO (PE) | 13.58 |
| Macrogel 400 - Polyethylene glycol 400 | 6.61 |
| Methocel E5 - hypromellose | 19.73 |
| Methocel E3 - hypromellose | 27.1 |
| Polyethylene Oxide N80 | 4.47 |
| Carbopol 974P | 1 |
| Sodium hydroxide (weight in comp 2.00N 8% (W/v)) | 2.92 |
| Lansoprazole | 19.49 |

(PE)—Permeation Enhancer

Water Permeable First Layer (Expressed in % M/M Dry weight)

| Component | Quanity % (w/w) |
|---|---|
| TiO2 | 4.02 |
| Methocel K4M - hypromellose | 1.51 |
| Methocel E50 - hypromellose | 5.03 |
| Polyethylene Oxide N80 | 2.51 |
| Kollicoat SR 30 | 69.35 |
| Maltodextrin (M100) | 7.54 |
| Propylene glycol | 10.05 |

(PE)—Permeation Enhancer

The Inventors were able to produce the first and second water soluble drug layers as solid solutions. A first drug delivery device (variant 1) was formed for later testing by laminating the first water soluble drug layer films to the water permeable first layer and then cut into a size of 22×22 mm that weighed 150 mg. In the first drug delivery device the water soluble active layer made up about 73% of the weight of the device while the water permeable first layer made up about 27% of the weight of the device.

A second drug delivery device (variant 2) was formed for later testing by laminating the second water soluble drug layer films to the water permeable first layer and then cut into a size of 22×22 mm that weighed about 120 mg. In the second drug delivery device the water soluble active layer made up about 67% of the weight of the device while the water permeable first layer made up about 33% of the weight of the device.

Figure 8:
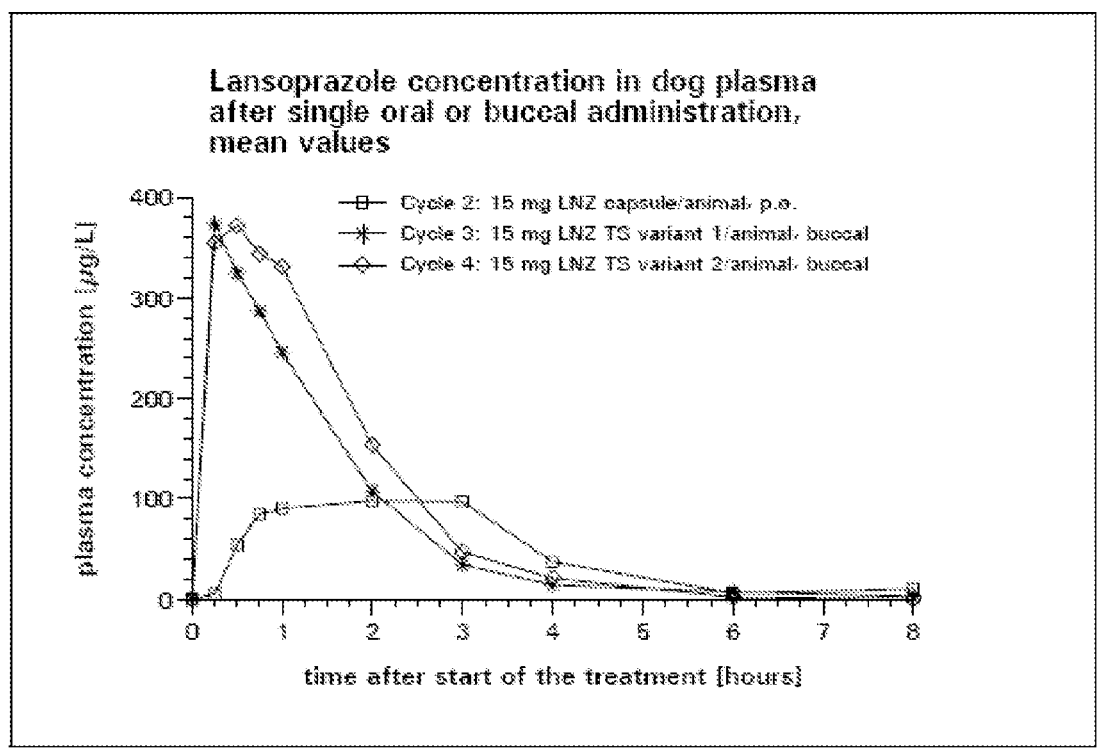

As shown in FIG. 8, testing of both the first and the second buccal drug delivery devices (variant 1 and 2) in canine subjects indicated that the buccal administration using either device resulted in significantly more rapid buildup of the drug to high levels in the blood stream (e.g. plasma) as compared to oral administration of capsule (LNZ capsule) containing the same amount of enteric coated drug to a canine. Furthermore, the initial test showed that therapeutic levels of the drug in the blood stream are maintained for several hours. The results are special in at least two ways. The first is that the time until the max concentration of drug in blood plasma was thirty minutes or less (e.g. 15 minutes or less). Second, the amount of concentration of the drug in blood plasma was much higher than expected. Thus, in one embodiment, the active layer preferably comprises lansoprazole and a base stabilizer.

Illustration 2: In vitro Testing 2.1 Summary

Both layers of a bilayer buccal film were currently made by a solution casting process. The formulas are initially made in a homogenous liquid mix using water and acetone as the solvents. The liquid mixes are coated onto a liner to a uniform wet thickness and then dried to the desired moisture content. The backing layer and the drug layer are made as separate films which are then laminated together. A Mathis labcoater LTE-S was used to coat and dry all films on 120# siliconized paper liners (Wausau GR421200).

A hand iron was used at low heat setting to laminate the drug and backing layers together. In this process, the backing layer was placed over the drug layer still on the non-stick coating liner. Another non-stick coating liner was placed on top of the backing layer and the iron was applied with moderate pressure and constant motion until the film layers were laminated together (~2-4 minutes). Laminating equipment exists that can perform this process faster and more consistently. Dyes, pigments, and flavors may be added to the backing layer to allow for easier discernment from the drug layer and to improve the taste.

The backing/water permeable layer includes:

(A) Kollicoat SR added as a 30% dispersion in water (30D)—(90% polyvinyl acetate, 9% povidone, and 1% lauryl sulfate) forms a water insoluble but swellable film through which water from the saliva can diffuse to hydrate the drug layer. In the case of this invention, the present Inventors have found that the Kollicoat SR hydrates and swells, while the soluble excipients dissolve leaving pores through which the drug layer film may be hydrated from saliva.

(B) HPMC (hypromellose)—Methocel E50, and Methocel K4M as a film strengthener and a pore former.

(C) Maltodextrin as a disintegrant/pore former.

(D) Polyethylene Oxide as a plasticizer.

(E) Propylene Glycol as a plasticizer.

The backing layer keeps the drug layer in intimate contact with the buccal tissue, maintains high drug concentrations, and slows the disintegration of the drug layer.

The water soluble drug layer includes:
(A) Lansoprazole at 15 mg per dose in a solid solution homogenously distributed throughout the film.
(B) HPMC (hypromellose)—Methocel E3, E5, and E50 a water soluble polymer/film former.
(C) Plasticizers/Humectants: Polyethylene Oxide and PEG 400 for film flexibility.
(D) pH modifier: Sodium hydroxide, for maintaining basic pH.
(E) Mucoadhesives: Proloc 25, Carbopol 974P, etc. to maintain intimate drug contact with oral mucosa.
(F) Permeation Enhancers: Menthol, DMSO, Sodium Glycocholate, Monoglycerides, Azone, and/or cyclodextrins.

The present Inventors have unexpectedly found that the drug layer keeps the lansoprazole (LNZ) localized during the film's disintegration because of the high viscosity of the hydrated gel. It also keeps the pH high and the drug dissolved while buccal delivery is occurring. Mucoadhesives and permeation enhancers are found to promote drug contact and absorption via the transcellular (across cell membranes) or paracellular (through the intercellular spaces) routes.

2.2 In Vitro Tests

In vitro buccal mucosa permeation studies were performed at 35° C. in glass static diffusion cells (0.2 cm² area) using buccal mucosa excised from the cheeks of pigs which did not undergo postmortem heat-treatment. Samples were kept frozen at −80° C.

Just prior to use, thawed mucosa samples were dermatomed to 0.8 mm and they were mounted horizontally on the Franz cells, dermis side down. The receptor phase of PBS pH 9.0 (phosphate buffered saline; 7.58 g/L $Na_2HPO_4$, 1.62 g/L $NaH_2PO_4$ and 4.4 g/L NaCl) with 20% methanol contained within each diffusion cell (approximately 4 ml) was mixed using a magnetic stirring. The permeation of tritiated water was first evaluated to determine the integrity of skins. Briefly, after a pre-equilibration period, 50 µl of tritiated water (2.7 µCi/ml) was applied to the surface. After 30 min, the radiolabelled water was removed from the mucosa with cotton tips. Then 2 ml from the receptor phase was taken in order to measure the amount of tritiated water (%) which permeated across the skin. Formulations were tested on sample skin having similar tritiated water permeation. A volume of 15 µl under non-occlusive conditions were applied on the mucosa. Samples of the receptor phase were collected at various time intervals: 0, 1, 3, 6 and 24 h. The removed receptor volume (1 ml) was replenished with fresh receptor solution after each withdrawal. Quantities of lansoprazole permeating the skin were determined by a HPLC analysis of the collected fractions just after sampling and ultracentrifugation at 13,000 rpm for 10 min before injecting in the HPLC. A total of at least 3 replicates were made per product.

2.3 Chromatographic Conditions

The chromotographic column was an Acquity HPLC© BEH C18 1.7 µm, 2.1×50 mm HPLC cartridge column. The mobile phase was a mixture of 5:3:2 (v/v/v) 0.05 M potassium dihydrogen phosphate, methanol, and acetonitrile filtered through a 0.20 µm nylon membrane filter. The flow rate was 0.25 ml/min and the injection volume was 10 µl and the column was set at 35° C. The separation was monitored at a wavelength of 280 nm. Quantification and validation was done with a freshly prepared standard curve. The standard references were prepared in PBS pH 7.4/methanol 80:20 and at least 90% of the drug remained after 24 h at 35° C. The standard curve covers concentrations found in the samples within a linear range.

2.4 Test Articles

Lansoprazole buccal film formulas were made and tested using the methods above. The target dose for each was 15 mg LNZ per 22 mm×22 mm (484 mm²) film. The main focus was on comparing different permeation enhancers, some attention was also given to solubilizing agents and mucoadhesives.

2.5 Backing Layer

For the in vitro testing, where a backing layer was used, it was mixed in the proportions shown in the following table.

| Material | Amt added (g) | Theoretical Film content (g) | % Film Weight |
|---|---|---|---|
| Acetone | 16.2 g | — | — |
| Methocel K4M | 0.42 g | 0.42 g | 1.5% |
| Kollicoat SR 30D | 80.96 g | 24.29 g | 89.5% |
| Propylene Glycol | 2.43 g | 2.43 g | 9.0% |
| Total | 100.01 g | 27.138 g | 100% |

The backing layer liquid mix was coated at 0.30 mm wet thickness, and dried at between 35-50° C. for 6.5-13 minutes in a Mathis labcoater LTE-S.

2.6 Drug Layer

For the in vitro testing, the two drug layers were made with permeation enhancers as shown in the following table. Film content of LNZ, HPMC, PolyOx N80, and PEG 400 were kept constant to specifically evaluate the effects of the different permeation enhancers, solubilizers, and mucoadhesives. The variability from target concentrations is inherent to the process of hand coating sheets.

TABLE

Drug layer Formulas.

| Enhancer/ Solubilizer/ Mucoadhesive | Enhancer qty/dose (mg) | LNZ qty/dose (mg) | HPMC[4] qty/dose (mg) | PolyOx N80 qty/dose (mg) | PEG 400 qty/dose (mg) | Liquid Mix Apparent pH | Lot # |
|---|---|---|---|---|---|---|---|
| Targets | as needed | 15.0 | 40 | 5 | 5 | 11.0 | N/A |
| Control | N/A | 15.5 | 41.3 | 5.2 | 5.2 | 11.1 | 1 |
| Menthol | 3.75 | 16.4 | 43.7 | 5.5 | 5.5 | 11.0 | 2 |
| Lutrol F-68, Cremophor | 15.0 15.0 | 15.0 | 39.9 | 5.0 | 5.0 | 11.0 | 3 |
| Azone:LNZ (1:2) | 7.5 | 15.1 | 40.2 | 5.0 | 5.0 | 11.0 | 4 |

TABLE-continued

Drug layer Formulas.

| Enhancer/ Solubilizer/ Mucoadhesive | Enhancer qty/dose (mg) | LNZ qty/dose (mg) | HPMC[4] qty/dose (mg) | PolyOx N80 qty/dose (mg) | PEG 400 qty/dose (mg) | Liquid Mix Apparent pH | Lot # |
|---|---|---|---|---|---|---|---|
| Azone:LNZ (1:1) | 14.7 | 14.7 | 39.3 | 4.9 | 4.9 | 11.0 | 5[5] |
| Azone:LNZ (2:1) | 30.8 | 15.4 | 41.1 | 5.1 | 5.1 | 11.0 | 6 |
| Monoglycerides[1] | 17.2 | 17.2 | 45.8 | 5.7 | 5.7 | 11.0 | 7 |
| NaGC[2] | 2.4 | 14.4 | 38.4 | 4.8 | 4.8 | 11.1 | 8 |
| Monoglycerides[1] | 14.4 | | | | | | |
| NaGC[2] | 2.6 | 15.6 | 41.7 | 5.2 | 5.2 | 11.0 | 9 |
| Monoglycerides[1] | 15.6 | | | | | | |
| Menthol | 15.6 | | | | | | |
| Arginine | 2.6 | | | | | | |
| NaGC[2] | 2.3 | 13.9 | 37.2 | 4.6 | 4.6 | 11.1 | 10 |
| Menthol | 13.9 | | | | | | |
| Arginine | 2.3 | | | | | | |
| DMSO | 14.4 | 14.4 | 38.5 | 4.8 | 4.8 | 11.1 | 11 |
| Noveon AA-1 | 0.1 | | | | | | |
| Methyl β-CD[3] | 47.7 | 14.8 | 39.5 | 4.9 | 4.9 | 11.0 | 12 |
| Methyl β-CD[3] | 20.4 | 13.6 | 36.3 | 4.5 | 4.5 | 11.0 | 13 |

[1]Monoglycerides (equal parts): Maisine 35-1, Capryol 90, Peceol, Capryol PGMC, Labrafac PG, & Labrasol.
[2]NaGC: Bile salt, sodium glycocholate
[3]Methyl β-CD: Methyl beta-Cyclodextrin, (Kleptose Crysmeb)
[4]HPMC: Methocel E3:Methocel E50, (3:1, Target- 30 mg:10 mg)
[5]This formula was not tested for in vitro permeation. Higher and lower Azone contents were tested.

2.7 In Vitro Permeation Results
2.7.1 Backing Layer Effects

Initial in vitro permeation testing compared three of the formulas from drug layer table above as monolayer and bilayer films. The Control formula (Lot 1, without permeation enhancers), the Menthol formula (Lot 2), and the Lutrol F-68, Cremophor formula (lot 3) were compared and shown in FIG. 4.

Figure 4:
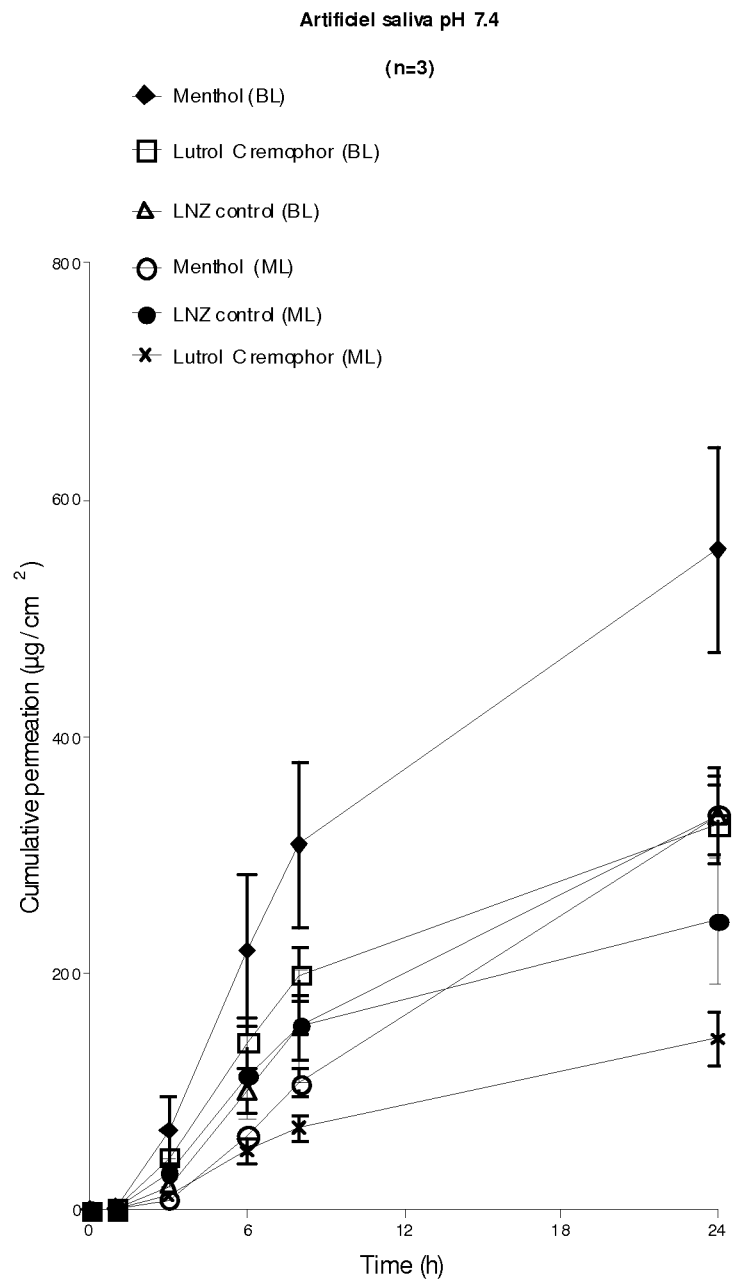
FIGS. 4-8 are graphical results from the Example Section.

FIG. 4 shows a comparison of in vitro permeation of formulas with and without backing layers. For each drug layer formula, the bilayer film exhibited higher permeation than the monolayer film. This demonstrated that the water permeable backing layer significantly improved buccal permeation over a simple oral-disintegrating film. This further supported the theory that the backing layer did in fact, keep the drug layer contained within a micro environment that was favorable for LNZ solubility and permeation.

The backing layer used in this study was an example of its functionality. Other variants and components for the backing layer may be used to exhibit similar or superior effects. The menthol films in this experiment showed the best permeation. Surprisingly, the Lutrol F-68 & Cremophor monolayer film seemed to exhibit an inhibitory effect compared to the Control monolayer film, and the bilayer film was equivalent to the control bilayer film. The menthol formula was superior to the other formulas and was tested in subsequent in vitro permeation testing for use as a baseline. This allowed for data normalization and comparisons between formulas analyzed on different days and using different tissue samples.

2.7.2 Permeation Enhancer Efficiency in Bilayer Films

The list of permeation enhancers attempted is not all inclusive. Other enhancers may exhibit equivalent or superior buccal permeation. The Menthol bilayer film was used as a baseline control to normalize for day-to-day assay and buccal tissue variability.

Figure 5:
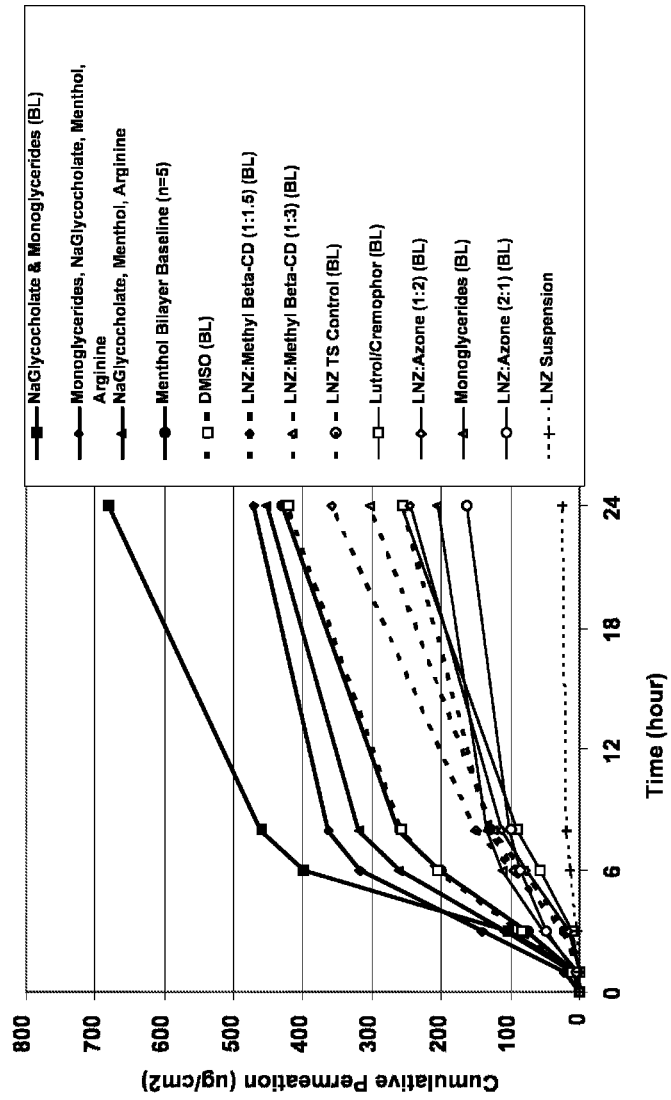
Figure 6:
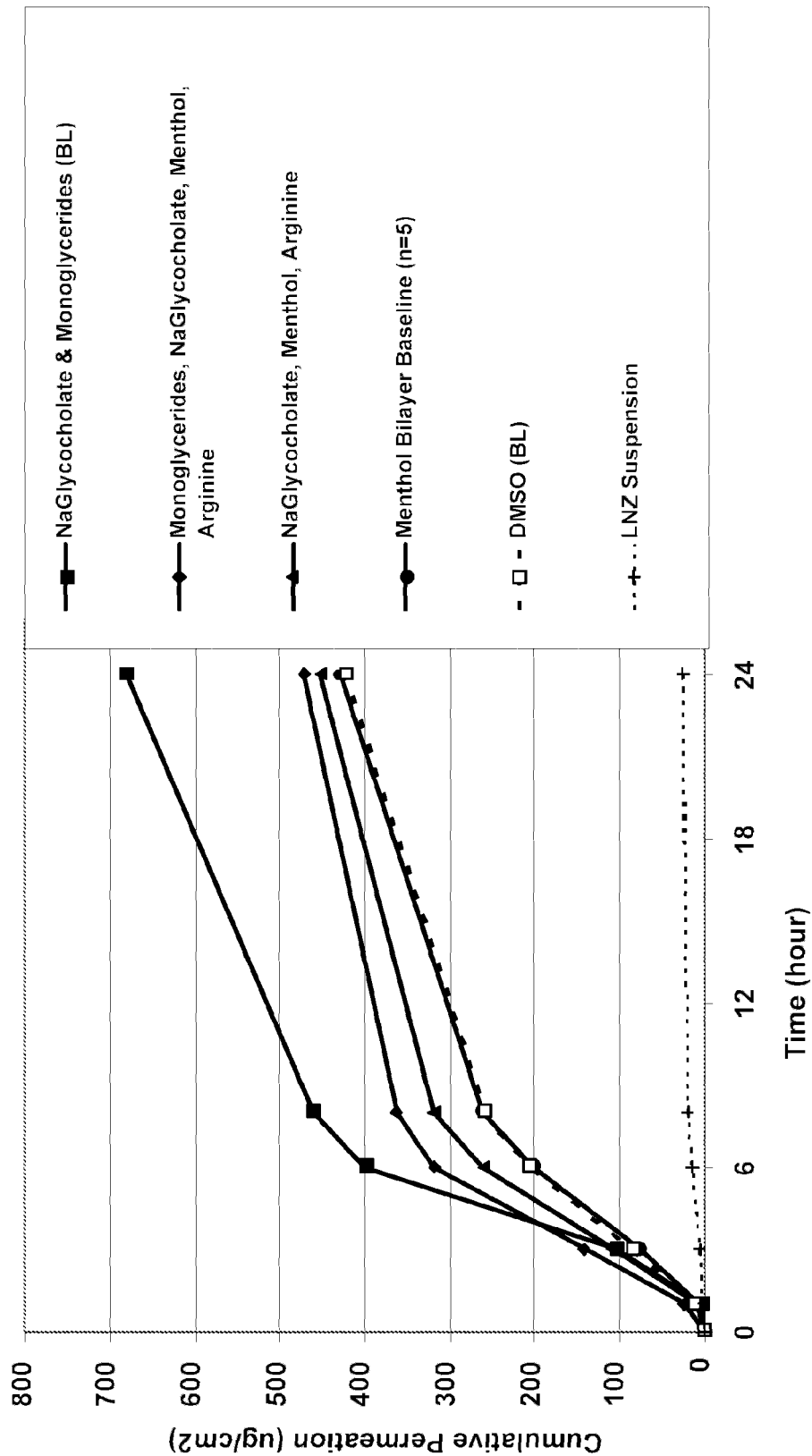

FIG. 5 shows in vitro permeation results of LNZ bilayer buccal films compared with a LNZ suspension control. Additionally, a 4 mg/mL LNZ suspension in artificial saliva was tested. The suspension was made by dissolving LNZ in methanol and diluting to 4 mg/mL in artificial saliva, pH 7.4. The 4 mg/mL concentration simulates a 15 mg dose disintegrated in approximately 4 mL of saliva. This suspension acted as a negative control, lacking the buccal film properties—pH, permeation enhancers, backing layer effects, etc. and revealed the drug's inherently poor buccal permeability properties under normal physiological conditions. From the results above, LNZ permeation from the bilayer buccal films increased by up to 29-times that of the drug suspension. FIG. 6 shows the permeation enhancers that exhibited the highest permeation.

2.7.3 Rinsing Effects (Saliva Washout/Swallowing Simulation)

In this experiment, the menthol bilayer film, the NaGC and Monoglyceride bilayer film, and the LNZ suspension were tested in the Franz cell. After three minutes of permeation, the donor phase in half of the Franz cells containing each test article was removed and the chamber rinsed. Fresh artificial saliva was added to replace the removed volume and the permeation allowed to continue. This testing simulated the swallowing action that would be expected in vivo, in the human mouth.

Figure 7:
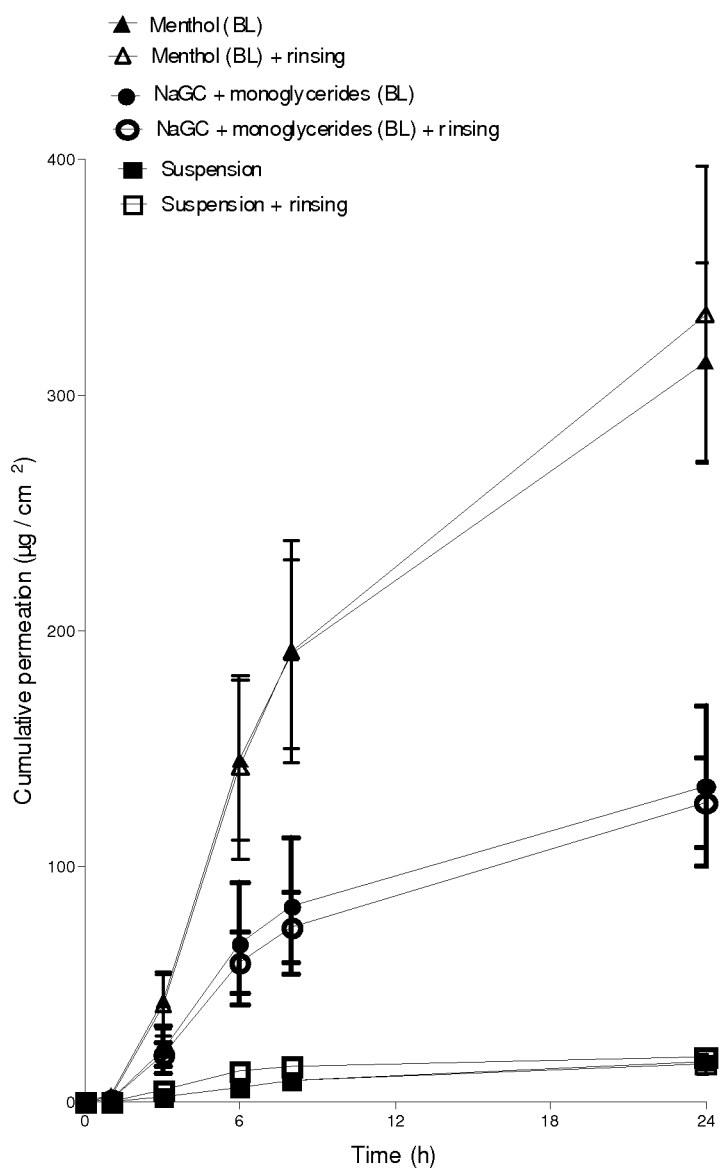

FIG. 7 shows in vitro permeation results of samples with and without rinsing. There was not an appreciable difference between the rinsed and un-rinsed films. This further demonstrates the protective nature of the backing layer and the proposed unidirectional flow of water through the backing layer into the drug layer. If the LNZ had significantly diffused through the backing layer into the donor chamber, the rinsing would have decreased the amount of permeation. The same phenomenon could be expected in the mouth as saliva is swallowed and fresh saliva is released to wet the mouth.

2.7.4 Expected pH of Disintegrated Films in Saliva

In this experiment, three monolayer films samples (1.6 cm$^2$) of several formulas were each disintegrated in the 2 mL of: water, artificial saliva, pH 7.4, or 50 mM NaOH (control). The disintegrated mixtures were allowed to stand for up to 4 hours to allow for precipitation of any supersaturated solutions. Each sample was then centrifuged at 20,000 rpm to remove precipitated or insoluble LNZ. Samples of each supernatant were diluted 10-fold (100 μL sample+900 μL) in 50 mM NaOH. The diluted samples were analyzed on a UV-VIS spectrophotometer at 292 nm in a 1-mm path-length cuvette. An extinction coefficient of 46.5 was used to calculate the concentration of each samples. The pH of the disintegrated samples was taken. Results are summarized in the table below.

Lansoprazole solubility and solution pH from monolayer films disintegrated in various solvents.

| Monolayer Film | | pH | | | LNZ Concentration (mg/mL) | | |
|---|---|---|---|---|---|---|---|
| Permeation Enhancer | Film Lot # | Artificial Saliva | Water | 50 mM NaOH | Artificial Saliva | Water | 50 mM NaOH |
| LNZ Control | 2871.40 | 7.9 | 9.4 | 11.6 | 0.29 | 2.29 | 2.29 |
| Menthol | 2871.42 | 7.9 | 9.6 | 11.6 | 0.31 | 2.13 | 2.23 |
| Lutrol F-68, Cremophor | 2871.44 | 7.9 | 9.5 | 11.6 | 0.25 | 1.99 | 2.07 |
| Azone:LNZ (1:2) | 2871.49A | 7.9 | 10.1 | 11.6 | 0.09 | 1.94 | 2.14 |
| Azone:LNZ (1:1) | 2871.50 | 7.9 | 10.0 | 11.6 | 0.25 | 1.90 | 2.03 |
| Azone:LNZ (2:1) | 2871.51 | 7.9 | 10.1 | 11.7 | 0.29 | 1.95 | 2.34 |
| Monoglycerides | 2877.03 | 8.1 | 9.9 | 11.6 | 0.09 | 2.11 | 2.29 |
| NaGC, Monoglycerides | 2877.05 | 8.0 | 9.9 | 11.7 | 0.07 | 2.03 | 2.36 |

From the results above, when the film is fully disintegrated in saliva, the pH of the mouth should be approximately 8. If a backing layer is used, the hydrated gel from the film will be trapped in a much smaller volume. The localized pH is expected to be around 10 shortly after the film is applied, and the pH slowly decrease to physiological ranges as the film disintegrates and disperses. Therefore, a higher drug concentration should be present until the film disperses.

The invention claimed is:

1. A layered drug delivery device having an outer side and an inner side, the device comprising in order from the outer side to the inner side:
   a first layer wherein the first layer is homogenous, water insoluble, water swellable, and water permeable when swelled, and
   a second layer comprising a therapeutic amount of a water soluble drug and a water soluble mucoadhesive film, said second layer disposed such that water passing through said first layer hydrates the second layer and solubilizes the drug, wherein said solubilized drug can permeate through a mucosal membrane when the inner side is in contact with the mucosal membrane,
wherein the drug delivery device is in sheet form, and
wherein the first layer and the second layer are in direct contact.

2. The layered drug delivery device of claim 1, wherein the water soluble drug comprises a proton pump inhibitor selected from the group consisting of: lansoprazole, omeprazole, esomeprazole, rabeprazole, pantoprazole, pariprazole, tentaprazole, and leminoprazole.

3. The layered drug delivery device of claim 2, wherein the water soluble drug comprises lansoprazole.

4. The layered drug delivery device of claim 3, further comprising a pH modifier in an amount sufficient to maintain a basic environment on the inner side of the device.

5. The layered drug delivery device of claim 1, wherein the second layer is a solid solution comprising the water soluble mucoadhesive film and the water soluble drug.

6. The layered drug delivery device of claim 5, wherein water passing through the first layer hydrates the second layer to solubilize the mucoadhesive film and the drug.

7. The layered drug delivery device of claim 1, further comprising a permeation enhancer disposed toward the inner side from the first layer.

8. The layered drug delivery device of claim 7, wherein the second layer is a solid solution comprising the permeation enhancer.

9. The layered drug delivery device of claim 7, wherein the permeation enhancer is contained in a separate layer disposed on the inner side from the first and second layers.

10. The layered drug delivery device of claim 1, wherein said first layer further comprises a pore former, wherein when the device is exposed to water the pore former dissolves to create a porous matrix in the first layer for water to travel through the first layer to hydrate the second layer.

11. The layered drug delivery device of claim 1, wherein the delivery device is 0.05 mm to 2.00 mm thick.

12. The layered drug delivery device of claim 11, wherein the delivery device is 0.1 mm to 1.00 mm thick.

13. The layered drug delivery device of claim 1, wherein the first layer makes up 10 wt % to 90 wt % of the drug delivery device and the second layer makes up 90 and 10 wt % of the drug delivery device.

14. The layered drug delivery device of claim 1,
   wherein the first layer is a film comprising:
      25 to 85 wt % of a film forming polymer composition, wherein the formed film is water insoluble, water swellable, and water permeable when swelled,
      1 to 75 wt % of a water soluble film forming agent,
      5 to 50 wt % of a pore forming agent, and
      1 to 20 wt % of a plasticizer selected from the group consisting of: glycerin, propylene glycol, triethyl citrate, and polyethylene glycol (PEG),
   wherein the second layer is a film of a solid solution comprising:
      1 to 50 wt % of a proton pump inhibitor selected from the group consisting of: lansoprazole, omeprazole, esomeprazole, rabeprazole, patoprazole, pariprazole, tentaprazole, and leminoprazole,
      1 to 75 wt % of a water soluble film forming agent,
      1 to 50 wt % of a water soluble mucoadhesive agent,
      1 to 50 wt % of a permeation enhancer,
      0.1 to 10 wt % of pH modifier, and
      1 to 20 wt % of a plasticizer selected from the group consisting of: glycerin, propylene glycol, triethyl citrate, and polyethylene glycol (PEG), said second film layer disposed such that water passing through said first film layer hydrates the second layer and solubilizes the proton pump inhibitor, wherein said solubilized lansoprazole can permeate through a mucosal membrane when the inner side is in contact with the mucosal membrane, wherein the drug delivery device is in sheet form.

15. The layered drug delivery device of claim 14, wherein the water insoluble, water swellable, and water permeable film forming polymer composition comprises a polyvinyl acetate polymer stabilized with povidone and sodium lauryl sulfate,
wherein the pore forming agent is a water soluble carbohydrate or water soluble hydrogenated carbohydrate,
wherein the permeation enhancer is selected from the group consisting of:
menthol, dimethyl sulfoxide (DMSO), sodium glycocholate, monoglycerides, azone, and cyclodextrins,
wherein the mucoadhesive compound is selected from the group consisting of:
a carboxy vinyl polymer that is cross-linked using an allyl ether of pentaerythritol as the cross linker, and
wherein the pH modifier is a base.

16. The layered drug delivery device of claim 14, wherein the water soluble film forming agent of the first sheet and the water soluble film forming agent of the second sheet, each comprise: a water soluble polyethylene oxide polymer; a water soluble hypromellose polymer; or both a water soluble polyethylene oxide polymer and a water soluble hypromellose polymer,
wherein the polyethylene oxide polymer has a molecular weight of 70,000 to 300,000 daltons, and wherein when the water soluble hypromellose polymer is dispersed in water to form a 2 wt % solution, the solution has a viscosity measured at 20° C. of 1 centipoise to 100 centipoise.

17. The layered drug delivery device of claim 16, wherein the water soluble film forming agent of the first sheet comprises a water soluble polyethylene oxide polymer having a molecular weight about 200,000 daltons and a water soluble hypromellose polymer, wherein when the water soluble hypromellose polymer is dispersed in water to form a 2 wt % solution, the solution has a viscosity measured at 20° C. of 50 centipoise to 100 centipoise, and
wherein the water soluble film forming agent of the second sheet comprises a water soluble polyethylene oxide polymer having a molecular weight about 200,000 daltons and a water soluble cellulose ether polymer, wherein when the water soluble hypromellose polymer is dispersed in water to form a 2 wt % solution, the solution has a viscosity measured at 20° C. of 1 centipoise to 10 centipoise.

18. A layered film drug deliver device having an outer side and an inner side, the device comprising films in order from the outer side to the inner side:

(i) a first film layer wherein the first layer is homogenous, water insoluble, water swellable, and water permeable, wherein the first layer comprises:
54 to 63 wt % of a water insoluble, water swellable, and water permeable film forming polymer composition comprising a polyvinyl acetate polymer stabilized with povidone and sodium lauryl sulfate,
6 to 19 wt % of a water soluble film forming agent comprising a water soluble polyethylene oxide polymer and a water soluble hypromellose polymer, wherein the polyethylene oxide polymer has a molecular weight of 70,000 to 300,000 daltons, and wherein when the water soluble hypromellose polymer is dispersed in water to form a 2 wt % solution, the solution has a viscosity measured at 20° C. of 1 centipoise to 100 centipoise,
10 to 15 wt % of a pore forming agent selected from the group consisting of water soluble carbohydrate, water soluble hydrogenated carbohydrate, or a combination thereof, and
8 to 12 wt % of a plasticizer selected from the group consisting of glycerin, propylene glycol, and polyethylene glycol (PEG),
(ii) a second film layer comprising:
14 to 20 wt % lansoprazole,
35 to 50 wt % of a water soluble film forming agent comprising a water soluble polyethylene oxide polymer and a water soluble hypromellose polymer, wherein the polyethylene oxide polymer has a molecular weight of 70,000 to 300,000 daltons, and wherein when the water soluble hypromellose polymer is dispersed in water to form a 2 wt % solution, the solution has a viscosity measured at 20° C. of 1 centipoise to 100 centipoise,
1 to 5 wt % of a water soluble mucoadhesive,
15 to 30 wt % of a permeation enhancer,
2.5 to 5 wt % NaOH, and
5 to 7 wt % of a polyethylene glycol having a molecular weight of 100 to 1000 dalton,
said second film layer being present as a solid solution and disposed such that water passing through said first film layer hydrates the second layer and solubilizes the lansoprazole, wherein said solubilized lansoprazole can permeate through a mucosal membrane when the inner side is in contact with the mucosal membrane,
wherein the drug delivery device is in sheet form, and
wherein the first layer and the second layer are in direct contact.

19. The layered drug delivery device of claim 1, wherein the first layer and the second layer are laminated together.

20. The layered drug delivery device of claim 18, wherein the first layer and the second layer are laminated together.

21. The layered drug delivery device of claim 1, further comprising a pH modifier in an amount sufficient to maintain a basic environment on the inner side of the device.

* * * * *